United States Patent [19]

Skötsch et al.

[11] Patent Number: 4,594,095

[45] Date of Patent: Jun. 10, 1986

[54] BIOCIDAL AZOLYL-PROPANE NITRILES

[75] Inventors: Carlo Skötsch; Dietrich Baumert; Hansjörg Krähmer, all of Berlin, Fed. Rep. of Germany

[73] Assignee: Schering Aktiengesellschaft, Berlin and Bergkamen, Fed. Rep. of Germany

[21] Appl. No.: 640,156

[22] Filed: Aug. 10, 1984

[30] Foreign Application Priority Data

Aug. 10, 1983 [DE] Fed. Rep. of Germany ....... 3329213

[51] Int. Cl.$^4$ .................. A01N 43/50; A01N 43/653; C07D 233/61; C07D 249/08
[52] U.S. Cl. ........................................ 71/92; 514/383; 514/399; 548/262; 548/341
[58] Field of Search ................ 548/341, 262; 514/399, 514/383; 71/92

[56] References Cited

U.S. PATENT DOCUMENTS 4,073,921 2/1978 Miller et al. .................... 548/341 X

FOREIGN PATENT DOCUMENTS 2604047 9/1976 Fed. Rep. of Germany ...... 548/341
3125780 1/1983 Fed. Rep. of Germany ...... 548/341

OTHER PUBLICATIONS

March, J., Advanced Organic Chemistry, McGraw Hill, New York, 1968, pp. 331 and 335.

Primary Examiner—Richard A. Schwartz
Attorney, Agent, or Firm—Michael J. Striker

[57] ABSTRACT

Azolyl-propanenitriles are disclosed, of the formula

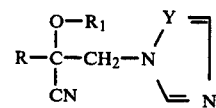

in which

R is an aromatic hydrocarbon or an aromatic hydrocarbon substituted one or more times, the same or differently by halogen, ($C_1$–$C_4$)-alkyl, ($C_1$–$C_4$)-alkoxy, trifluoromethyl, cyano or nitro, $R_1$ is $C_3$–$C_8$ cycloalkyl or $C_3$–$C_8$ cycloalkyl substituted by $C_1$–$C_3$ alkyl and Y is N or CH, and its acid addition salt with an inorganic or an organic acid, as well as processes for the production of these compounds and biocidal compositions containing the same. The compounds display fungicidal activity, growth-regulatory activity, and bactericidal activity.

12 Claims, No Drawings

BIOCIDAL AZOLYL-PROPANE NITRILES

BACKGROUND OF THE INVENTION

The invention concerns new azolyl-propane nitriles, processes for the production of these compounds, as well as biocidal compositions containing the same, and particularly those with fungicidal activity.

PATENT DISCLOSURE STATEMENT

Imidazolyl-propionitrile derivatives with fungicidal activity are already known (DE-OS No. 26 04 047). However, these compounds display a relatively narrow activity spectrum which is unsatisfactory.

Imidazolyl-propionitriles with biocidal activity are likewise already known (DE-OS No. 31 25 780). Despite their fairly good effectiveness, there remains a need for compounds with still better characteristics.

OBJECT AND SUMMARY OF THE INVENTION

It is therefore an object according to the present invention to develop new propionitrile derivatives which open up broadly multiplied use possibilities, particularly in the field of plant protection, and which provide greater fungicidal activity.

This object is obtained according to the present invention by azolyl-propane nitriles of the general formula $$R-\underset{\underset{CN}{|}}{\overset{\overset{O-R_1}{|}}{C}}-CH_2-N\begin{pmatrix}Y=\\ \\ =N\end{pmatrix} \quad I$$

in which
- R is an aromatic hydrocarbon or an aromatic hydrocarbon substituted at least once by the same or by different $(C_1-C_4)$-alkyl, $(C_1-C_4)$-alkoxy, trifluoromethyl, cyano or nitro $R_1$ is $C_3-C_8$-cycloalkyl or $C_3-C_8$-cycloalkyl substituted by $C_1-C_3$-alkyl radicals and
- Y is N or CH, and their acid addition salts with inorganic or organic acid.

The compounds according to the present invention are in the broadest sense biocidally effective. They are characterized however, in particular by a fungicidal activity which, in a surprising manner, exceeds that of known active substances of analogous constitution and activity.

The fungicidal activity, surprisingly, is effective against fungi having the most different systematic structures. Used in treatment of above-ground plant parts, they protect against wind borne pathogens. The compounds also can be employed for the treatment of seed goods against seed-transportable pathogens. Moreover, they work systematically, that is, they are withdrawn by the roots of the plants, for example, after application during the sowing, and are then transported into the above-ground parts of the plants to protect the same against pathogens.

As further activities characteristic of the compounds according to the present invention, mention may be made of their growth-regulatory and bactericidal activities.

Because of their broad activity spectrum, the compounds according to the present invention are suitable not only for the protection of so-called culture plants but also for the protection of materials and for the control of human pathogenic and animal pathogenic microbes, and therefore exhibit broadly multiplied use possibilities. Depending upon the presence of specific substituents, the compounds according to the present invention display various outstanding activity. Thus, the compounds can be employed as fungicides, and plant-growth regulators. The compounds according to the present invention also find use as plant-growth regulators which are characterized, for example, by the following use possibilities:

Reduction in the vegetative growth of woody and weed plants, for example, at road borders, railroad plants and the like, in order to prevent too abundant a growth. Reduction in growth grain in order to prevent depositing or breaking-off; and with cotton, in order to increase the yield.

Influencing the branching of vegetative and generative organs with ornamental or culture plants, in order to multiply the onset of blooming; or with tobacco and tomato in order to reduce the development of sideshoots.

Improvement of the fruit quality, for example, increasing the sugar content of sugar beets, sugar cane or fruit; and a more uniform ripening of the harvest goods, which leads to higher yields.

Increasing the resistance against climatic influences such as cold and dryness.

Influencing the latex flow of rubber plants.

Formation of parthenocarpic fruit, pollen sterility and sexual influence are likewise possibilities of use.

Control of the germination of seeds or the driving out of buds.

Defoliation or influencing the fruit fall in order to facilitate harvesting.

The compounds according to the present invention are suitable in particular for influencing the growth of beta beets. They also display desirable growth-regulatory effects with grain, soybeans and cotton.

The amounts of active compounds, depending upon specific use applied, range generally from 0.05 up to 5 kg of active substance per hectare. However, if necessary even higher application amounts can be employed.

The time of employment depends upon purpose of use and the climatic conditions.

In the compounds of general formula I, the substituents can represent, for example:
R is 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl 2,4-dichlorophenyl, 3,4-dichlorophenyl, 2,6-dichlorophenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl 2-isopropyphenyl, 3-isopropylphenyl, 4-isopropylphenyl, 2-butylphenyl, 3-butylphenyl, 4-butylphenyl, 2-sec-butylphenyl, 3-sec-butylphenyl, 4-sec-butylphenyl, 2-tert-butylphenyl, 3-tert-butylphenyl, 4-tert-butylphenyl, 2-methoxyphenyl, 3-methoxyphenyl, 4-methoxyphenyl, 2-ethoxyphenyl, 3-ethoxyphenyl, 4-ethoxyphenyl, 2-methylthiophenyl, 3-methylthiophenyl, 4-methylthiophenyl, 2-ethylthiophenyl, 3-ethylthiophenyl, 4-ethylthiophenyl 2-trifluromethylphenyl, 3-trifluormethylphenyl, 4-trifluromethylphenyl, 2-nitrophenyl, 3-nitrophenyl, 4-nitrophenyl, 3-fluoro-4-methoxyphenyl, 3,4,5-trimethoxyphenyl, 5-chloro-2-nitrophenyl, 3-chloro-5-nitro phenyl or 4-chloro-2-fluorophenyl $R_1$ can be cyclopropyl, cyclobutyl, cyclopentyl, cyclohexyl, cycloheptyl, cyclooctyl, 2-methylcyclopentyl, 2-methylcyclohexyl, 2,2-dimethylcyclopentyl, or 2,2-dimethylcyclohexyl and Y is N or CH.

Not only inorganic acids but organic acids can be used to form the acid addition salts. These include the following:

hydrochloric acid and hydrobromic acid, phosphoric acid, sulfuric acid, particularly nitric acid, mono- and bi-functional carboxylic acid and hydroxycarboxylic acids, such as, for example, acetic acid, maleic acid, succinic acid, fumaric acid, tartaric acid, citric acid, salicylic acid, sorbic acid, lactic acid, as well as sulfonic acids such as for example, p-toluene sulfonic acid and 1,5-naphthalene disulfonic acid.

The acid addition salts can be formed by customary salt formation techniques, for example, by dissolving a compound of formula I in a suitable solvent and then adding the acid.

An outstanding fungicidal activity is displayed for example, by the following compounds:

2-(4-chlorophenyl)-2-cyclopentyloxy-3-(imidazol-1-yl)-propanenitrile and the hydronitrate; 2-(4-chlorophenyl)-2-cyclopentyloxy-3-(1,2,4-triazol-1-yl)-propanenitrile and the hydronitrate; 2-cyclopentyloxy-3-(imidazol-1-yl)-2-(2-methylphenyl)-propanenitrile and the hydronitrate; 2-cyclopentyloxy-2-phenyl-3-(1,2,4-triazol-1-yl)-propanenitrile, and the hydronitrate; 2-(2-chlorophenyl)-2-cyclopentyloxy-3-(1,2,4-triazol-1-yl)-propane-nitrile and the hydronitrate; 2-cyclopentyloxy-3-(imidazol-1-yl)-2-phenyl-propanenitrile, and the hydronitrate.

Aside from the above-designated activities, the compounds according to the present invention also are bactericidal which allows further possibilities of employment.

The compounds according to the present invention can be used either alone or in mixture with one another or with other active substances. If necessary, other plant-protection or pest-control agents can be added, according to the desired purpose.

The active substances of the invention or their mixtures are employed in the form of preparation such as powders, spray agents, granulates, solutions, emulsions or suspensions, with the addition of liquid and/or solid carrier material, respectively, diluting agents and, if necessary, wetting, adhering, emulsifying and/or dispersing adjuvants.

Suitable liquid carrier substances include, for example, water, aliphatic and aromatic hydrocarbons, such as benzene, toluene, xylene, cyclohexanone, isophorone, dimethylsulfoxide, dimethylformamide, moreover, mineral oil fractions and plant oils.

Suitable as solid carrier materials are mineral earths, for example tonsil, silica gel, talcum, kaolin, attapulgite, limestone, silicic acid and plant products, for example, meal.

Examples of surface-active substances include: calcium lignin sulfonate and their salts, formaldehyde condensate, fatty alcohol sulfate, as well as substituted benzene sulfonic acids and their salts.

Insofar as the active substances are supposed to be employed for disinfection of seed goods, dyes can be admixed in order to provide the pickledseed goods with a clearly visible coloration.

The portion of the active substance in the various preparations can range within broad limits. For example, the composition can contain from about 10 to 90 percent by weight active substance, about 90 to 10 percent weight liquid or solid carrier material, as well as, if necessary, up to 20 percent by weight of surface-active substance, upon corresponding reduction in the amount of carrier.

The present composition can be applied in known manner, for example, with water as the carrier in spray amounts of about 100 up to about 10,000 liter/ha. The compositions also can be used in the so-called low-volume or ultra-low-volume techniques, and in the form of microgranulates.

By way of non-limiting examples, the following typify the compounds of the invention.

A. Spray Powder (a)
40 percent by weight active substance
25 percent by weight clay mineral
20 percent by weight silicic acid
10 percent by weight cell pitch
5 percent by weight surface-active substance based upon a mixture of the calcium salt of lignin sulfonic acid, alkylphenolpolyglycolether (b)
20 percent by weight active substance
60 percent by weight kaolin
15 percent by weight silicic acid
5 percent by weight surface-active substance based upon the sodium salt of N-methyl-N-oleyltaurine and the calcium salt of lignin sulfonic acid (c)
10 percent by weight active substance
60 percent by weight clay minerals
15 percent by weight silicic acid
10 percent by weight cell pitch
5 percent by weight surface-active substance based upon the sodium salt of N-methyl-N-oleyltaurine and the calcium salt of lignin sulfonic acid

B. Paste 45 percent by weight active substance
5 percent by weight sodium aluminum silicate
15 percent by weight cetylpolyglycolether with 8 mol ethylenoxide
2 percent by weight spindle oil
10 percent by weight polyethyleneglycol
23 parts water

C. Emulsion Concentrate 25 percent by weight active substance
15 percent by weight cyclohexanol
55 percent by weight xylene
5 percent by weight mixture of nonylphenylpolyoxyethylene or calcium dodecylbenzene sulfonate The new compounds according to the present invention can be produced by reacting compounds of the general formula

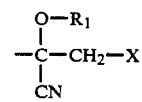

with compounds of the general formula

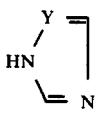

or their alkali salts in the presence of a solvent and, if necessary, in the presence of a base, whereby R, $R_1$ and Y have the above given meaning, and X is halogen, alkylsulfonyloxy or arylsulfonyloxy, or alkylsulfonyloxy or arylsulfonyloxy halogenated in a side chain.

Examples of halogen include chlorine, bromine or iodine; methyl, ethyl, propyl and trifluoromethylsulfonyl are suitable as alkylsulfonyloxy; whereas examples of arylsulfonyloxy include benzene sulfonyloxy and p-toluene sulfonyloxy.

When a solvent is employed it is desirable to select a material which is inert with respect to the reactants, preferably polar, aprotic substances such as N,N-dimethylformamide, N-methylpyrrolidone, tetramethylurea, hexamethylphosphoric acid triamide and dimethylsulfoxide, and even higher boiling aromatic and aliphatic hydrocarbons such as toluene, fluorobenzene, or xylene. The reaction temperature can be varied within broad limits. Preferably a temperature between 100° C. and 200° C. is used. The reactions follow under normal or excess pressure.

The novel features which are considered as characteristics of the invention are set forth in particular in the appended claims. The invention itself, however, both as to its construction and its method of operation, together with additional objects and advantages thereof, will be best understood from the following description of specific embodiments.

DESCRIPTION OF PREFERRED EMBODIMENTS

Example 1

2-cyclopentyloxy-3-(imidazol-1-yl)-2-(methylphenyl)-propanenitrile, hydronitrate 60.7 g (0.188 mol) 2-cyclopentyloxy-2-(2-methylphenyl)-3-methylsulfonyloxy-propanenitrile, 63.9 g (0.938 mol) imidazole and 3.88 ml DMF are stirred for six hours at 160° C. bath temperature. They are then poured into 200 ml water, extracted twice—each time with 200 ml methylene chloride—and the organic phase is then dried with MgSO$_4$. It is then rotated in a vacuum after which the oil is dissolved in 100 ml isopropanol and then reacted dropwise with 10 ml 100% nitric acid, with cooling with ice. Next follows 20 minutes afterstirring with RT, addition of 200 ml acetic ester, and evacuation in a vacuum. In this manner 30.7 g of the title compound are obtained, MP: 160° C. (decomposition).

Example 2

2-cyclopentyloxy-3-(imidazol-1-yl)-2-(methylphenyl)-propanenitrile 28.5 g of the hydronitrate obtained in Example 1 are dissolved in 300 ml methanol. Within a period of 5 minutes and at a temperature of between 5° and 15° C., 100 ml dilute ammonia solution are added dropwise. The mixture is then diluted with 750 ml water and extracted twice, each time with 300 ml ethyl acetate. Then follows drying with MgSO$_4$, centrifuging to dryness, and reaction of the remaining oil with 200 ml hexane, whereafter crystallization occurs. In this manner are obtained 21.7 g of the title compound, MP: 92° C.

Example 3

2-cyclohexyloxy-2-(2-methylphenyl)-3-(1,2,4-triazol-1-yl)-propanenitrile, hydronitrate 9.8 g of 1,2,4-triazol are heated in a mixture of 120 ml dimethylsulfoxide and 70 ml xylene with 5.7 g NaOH-tablets for two hours at 180° C. bath temperature. Reaction water is removed in a water separator. The bath temperature is then allowed to drop to 150° C., and 32 g of 2-cyclohexyloxy-3-methansulfonyl-2-(2-methylphenyl)-propanenitrile and a little DMSO are added to the reaction mixture. After stirring for three hours at 150° C., ice-water is aded, followed by two extractions, each time with 200 ml methylene chloride, whereupon the organic phase is washed again with 100 ml H$_2$O. Then follows drying with MgSO$_4$, spinning, take up in 70 ml isopropanol and dropwise reaction under ice cooling with 3.9 ml. 100% nitric acid. The reaction mixture is then reacted with 50 ml ether, evacuated in a vacuum and then recrystallized from isopropanol. 14.36 g of the title compound are obtained, with melting point 194°–197° C. (decomposition).

In analogous manner, using appropriate starting materials the following compounds according to the present invention are prepared:

| Example | Name of Compound | Physical Constant |
|---|---|---|
| 4 | 2-cyclopentyloxy-2-(2-methylphenyl)-3-(1,2,4-triazol-1-yl)-propanenitrile, hydeonitrate | MP: 142–144° C. (D) |
| 5 | 2-cyclohexyloxy-3-(imidazol-1-yl)-2-(2-methylphenyl)-propanenitrile, hydronitrate | MP: 150–152° C. (D) |
| 6 | 2-cyclohexyloxy-3-(imidazol-1-yl)-2-(2-methylphenyl)-propanenitrile | MP: 114–116° C. |
| 7 | 2-cyclohexyloxy-2-(2-methylphenyl)-3-(1,2,4-triazol-1-yl)-propanenitrile | MP: 82–85° C. |
| 8 | 2-cyclohexyloxy-3-(imidazol-1-yl)-2-phenyl-propanenitrile | MP: 75° C. |
| 9 | 2-cyclohexyloxy-3-(imidazol-1-yl)-2-phenyl-propanenitrile, hydronitrate | MP: 211–212° C. (D) |
| 10 | 2-(2-chlorophenyl)-2-cyclohexyloxy-3-(imidazol-1-yl)-propanenitrile | MP: 128° C. |
| 11 | 2-(2-chlorophenyl)-2-cyclohexyloxy-3-(imidazol-1-yl)-propanenitrile, hydronitrate | MP: 186–188° C. (D) |
| 12 | 2-cyclohexyloxy-2-phenyl-3-(1,2,4-triazol-1-yl)-propanenitrile | MP: 94–97° C. |
| 13 | 2-cyclohexyloxy-2-phenyl-3-(1,2,4-triazol-1-yl)-propanenitrile, hydronitrate | MP: 185–186° C. (D) |
| 14 | 2-(4-chlorophenyl)-2-cyclohexyloxy-3-(imidazol-1-yl)-propanenitrile, hydronitrate | MP: 214–215° C. (D) |
| 15 | 2-(2-chlorophenyl)-2-cyclohexyloxy-3-(1,2,4-triazol-1-yl)-propanenitrile | MP: 109–112° C. |
| 16 | 2-(2-chlorophenyl)-2-cyclohexyloxy-3-(1,2,4-triazol-1-yl)-propanenitrile, hydronitrate | MP: 139° C. (D) |
| 17 | 2-cyclopentyloxy-3-(imidazol-1-yl)-2-phenyl-propanenitrile | $n_D^{20}$: 1.5462 |
| 18 | 2-cyclopentyloxy-3-(imidazol-1-yl)-2-phenyl-propanenitrile, hydronitrate | MP: 164–167° C. (D) |

-continued

| Example | Name of Compound | Physical Constant |
|---|---|---|
| 19 | 2-(2-chlorophenyl)-2-cyclopentyloxy-3-(imidazol-1-yl)-propanenitrile | $n_D^{20}$: 1.5590 |
| 20 | 2-(2-chlorophenyl)-2-cyclopentyloxy-3-imidazol-1-yl)-propanenitrile, hydronitrate | MP: 130° C. (D) |
| 21 | 2-cyclopentyloxy-2-phenyl-3-(1,2,4-triazol-1-yl)-propanenitrile | MP: 85–88° C. |
| 22 | 2-cyclopentyloxy-2-phenyl-3-(1,2,4-triazol-1-yl)-propanenitrile, hydronitrate | MP: 172–174° C. |
| 23 | 2-(2-chlorophenyl)-2-cyclopentyloxy-3-(1,2,4-triazol-1-yl)-propanenitrile | MP: 91–94° C. |
| 24 | 2-(2-chlorophenyl)-2-cyclopentyloxy-3-(1,2,4-triazol-1-yl)-propanenitrile, hydronitrate | MP: 136° C. (D) |
| 25 | 2-cyclohexyloxy-2-(2,4-dichlorophenyl)-3-(imidazol-1-yl)-propanenitrile | $n_D^{20}$: 1.5565 |
| 26 | 2-cyclohexyloxy-2-(2,4-dichlorophenyl)-3-(imidazol-1-yl)-propanenitrile, hydronitrate | MP: 156° C. (D) |
| 27 | 2-(4-chlorophenyl)-2-cyclohexyloxy-3-(1,2,4-triazol-1-yl)-propanenitrile | MP: 97° C. (D) |
| 28 | 2-(4-chlorophenyl)-2-cyclohexyloxy-3-(1,2,4-triazol-1-yl)-propanenitrile, hydronitrate | MP: 176–178° C. (D) |
| 29 | 2-cyclohexyloxy-2-(2,4-dichlorophenyl)-3-(1,2,4-triazol-1-yl)-propanenitrile | MP: 121–124° C. |
| 30 | 2-cyclohexyloxy-2-(2,4-dichlorophenyl)-3-(1,2,4-triazol-1-yl)-propanenitrile, hydronitrate | MP: 145–148° C. (D) |
| 31 | 2-(4-chlorophenyl)-2-cyclopentyloxy-3-(imidazol-1-yl)-propanenitrile | MP: 100–102° C. |
| 32 | 2-(4-chlorophenyl)-2-cyclopentyloxy-3-(imidazol-1-yl)propanenitrile, hydronitrate | MP: 200–201° C. (D) |
| 33 | 2-(4-chlorophenyl)-2-cyclopentyloxy-3-(1,2,4-triazol-1-yl)-propanenitrile | MP: 89–92° C. |
| 34 | 2-(4-chlorophenyl)-2-cyclopentyloxy-3-(1,2,4-triazol-1-yl)-propanenitrile, hydronitrate | MP: 162–165° C. (D) |
| 35 | 2-cyclopentyloxy-2-(2-fluorophenyl)-3-(imidazol-1-yl)-propanenitrile | $n_D^{20}$: 1.5328 |
| 36 | 2-cyclopentyloxy-2-(2-fluorophenyl)-3-(1,2,4-triazol-1-yl)-propanenitrile | MP: 60–62° C. |
| 37 | 2-cyclohexyloxy-2-(2-fluorophenyl)-3-(imidazol-1-yl)-propanenitrile | $n_D^{20}$:1.5300 |
| 38 | 2-cyclohexyloxy-2-(2-fluorophenyl)-3-(1,2,4-triazol-1-yl)-propanenitrile | MP: 80–82° C. |
| 39 | 2-cyclopentyloxy-2-(2-fluorophenyl)-3-(imidazol-1-yl)-propanenitrile, hydronitrate | MP: 165–168° C. (D) |
| 40 | 2-cyclohexyloxy-2-(2-fluorophenyl)-3-(imidazol-1-yl)-propanenitrile, hydronitrate | MP: 205–206° C. (D) |
| 41 | 2-cyclopentyloxy-2-(2-methylphenyl)-3-(1,2,4-triazol-1-yl)-propanenitrile | MP: 78–81° C. |

(D) = Decomposition

The azolyl propanenitriles according to the present invention, as well as their acid addition salts, are nearly colorless and odorless oils or solids. The salts are slightly soluble in water but soluble in polar organic solvents such as acetonitrile, N,N-dimethylformamide, lower alcohols, chloroform and methylene chloride. The free bases dissolve poorly in water and more or less well in organic solvents such as, for example, alcohols, ethers or chlorinated hydrocarbons.

The starting materials, are 3-aryl-respectively 3-alkylsulfonyloxy-propanenitriles of the general formula II, with X representing aryl-respectively alkylsulfonyloxy have not previously been described in the literature. They are obtained by hydroxymethylating in known manner, already known phenyl acetonitriles of the general formula

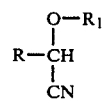

wherein R and $R_1$ have the above-given meanings, to obtain 3-hydroxypropanenitrile of the general formula

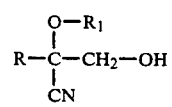

which are reacted with suitable sulfonic acid derivatives, such as, for example, sulfonic acid chloride, if necessary with the addition of an acid binder. The hydroxy methyl compounds of general formula IV were not previously disclosed in the literature. The phenylacetonitrile of the general formula III are obtained by reaction of O-sulfonated cyanohydrine with the corresponding alcohol $R_1OH$.

The following examples serve to illustrate various utilities for the compounds according to the present invention.

The actual concentration of the active substances used is given in ppm (parts per million of spray liquid). The fungicidal activity is calculated in the following Examples from infection data determined in each instance, as follows:

$$100 - \frac{\text{Infection in treated} \cdot 100}{\text{Infection in untreated}} = \% \text{ Activity}$$

Example 42

Effect of Prophylactic Leaf Treatment Against Real Mildew *Erysiphe graminis* on Barley in a Greenhouse.

Young barley plants in the stage of the first leaves are sprayed dripping wet with the given concentrations. After drying of the spray coating, the treated plants as well as untreated control plants are innoculated with dry mildew spores by stroking the test plants with infected plants. Thereafter the test plants are cultivated in a greenhouse at about 20°–22° C., and one week later the percentage of infection on the leaf surfaces is determined. The excellent activities of the compounds according to the present invention are evident from the following test data:

| Compound | % Activity Against *Erysiphe graminis* with Active Substance Concentration | | | |
|---|---|---|---|---|
| | 250 | 25 | 2.5 | ppm |
| 2-cyclopentyloxy-3-(imidazol-1-yl)-2-(2-methylphenyl)-propanenitrile, hydronitrate | 100 | 100 | 100 | |
| 2-cyclopentyloxy-2-(2-methylphenyl)-3-(1,2,4-triazol-1-yl)-propanenitrile, hydronitrate | 100 | 100 | 98 | |
| 2-cyclohexyloxy-3-(imidazol-1- | 100 | 100 | 100 | |

| Compound | % Activity Against Erysiphe graminis with Active Substance Concentration | | |
|---|---|---|---|
| | 250 | 25 | 2.5 ppm |
| yl)-2-(2-methylphenyl)-propanenitrile, hydronitrate | | | |
| 2-cyclohexyloxy-2-(2-methylphenyl)-3-(1,2,4-triazol-1-yl)-propanenitrile, hydronitrate | 100 | 100 | >90 |
| 2-cyclohexyloxy-3-(imidazol-1-yl)-2-(2-methylphenyl)-propanenitrile | 100 | 100 | 100 |
| 2-cyclohexyloxy-2-(2-methylphenyl)-3-(1,2,4-triazol-1-yl)-propanenitrile | 100 | 100 | >90 |
| 2-cyclopetyloxy-3-(imidazol-1-yl)-2-(2-methylphenyl)-propanenitrile | 100 | 100 | 100 |
| 2-cyclopentyloxy-2-(2-methylphenyl)-3-(1,2,4-triazol-1-yl)-propanenirile | 100 | 100 | 100 |
| 2-cyclohexyloxy-3-(imidazol-1-yl)-2-phenyl-propanenitrile | 100 | 100 | 100 |
| 2-cyclohexyloxy-3-(imidazol-1-yl)-2-phenyl-propanenitrile, hydronitrate | 100 | 100 | 100 |
| 2-(2-chlorophenyl)-2-cyclohexyloxy-3-(imidazol-1-yl)-propanenitrile | 100 | 100 | 95 |
| 2-(2-chlorophenyl)-2-cyclohexyloxy-3-(imidazol-1-yl)-propanenitrile, hydronitrate | 100 | 100 | 100 |
| 2-cyclohexyloxy-2-phenyl-3-(1,2,4-triazol-1-yl)-propanenitrile | 100 | 100 | 87 |
| 2-cyclohexyloxy-2-phenyl-3-(1,2,4-triazol-1-yl)-propanenitrile, hydronitrate | 100 | 100 | 100 |
| 2-(4-chlorophenyl)-2-cyclohexyloxy-3-(imidazol-1-yl)-propanenitrile, hydronitrate | 100 | 100 | 100 |
| 2-(2-chlorophenyl)-2-cyclohexyloxy-3-(1,2,4-triazol-1-yl)-propanenitrile | 100 | 100 | 100 |
| 2-(2-chlorophenyl)-2-cyclohexyloxy-3-(1,2,4-triazol-1-yl)-propanenitrile, hydronitrate | 100 | 100 | 100 |
| 2-cyclopentyloxy-3-(imidazol-1-yl)-2-phenyl-propannitrile | 100 | 100 | 95 |
| 2-cyclopentyloxy-3-(imidazol-1-yl)-2-phenyl-propanenitrile, hydronitrate | 100 | 100 | 100 |
| 2-(2-chlorophenyl)-2-cyclopentyloxy-3-(imidazol-1-yl)-propanenitrile | 100 | 100 | 100 |
| 2-(2-chlorophenyl)-2-cyclopentyloxy-3-(imidazol-1-yl)-propanenitrile, hydronitrate | 100 | 100 | 100 |
| 2-cyclopentyloxy-2-phenyl-3-(1,2,4-triazol-1-yl)-propanenitrile | 100 | 100 | 100 |
| 2-cyclopentyloxy-2-phenyl-3-(1,2,4-triazol-1-yl)-propanenitrile, hydronitrate | 100 | 100 | 100 |
| 2-(2-chlorophenyl)-2-cyclopentyloxy-3-(1,2,4-triazol-1-yl)-propanenitrile | 100 | 100 | 87 |
| 2-(2-chlorophenyl)-2-cyclopentyloxy-3-(1,2,4-triazol-1-yl)-propanenitrile, hydronitrate | 100 | 100 | - |
| 2-cyclohexyloxy-2-(2,4-dichlorophenyl)-3-(imidazol-1-yl)-propanenitrile | 100 | 100 | 87 |
| 2-cyclohexyloxy-2-(2,4-dichlorophenyl)-3-(imidazol-1-yl)-propanenitrile, hydronitrate | 100 | 100 | 88 |
| 2-(4-chlorophenyl)-2-cyclohexyloxy-3-(1,2,4-triazol-1-yl)-propanenitrile | 100 | 100 | 100 |
| 2-(4-chlorophenyl)-2-cyclohexyloxy-3-(1,2,4-triazol-1-yl)-propanenitrile, hydronitrate | 100 | 100 | 94 |
| 2-cyclohexyloxy-2-(2,4-dichlorophenyl)-3-(1,2,4-triazol-1-yl)-propanenitrile | 100 | 100 | 100 |
| 2-cyclohexyloxy-2-(2,4-dichlorophenyl)-3-(1,2,4-triazol-1-yl)-propanenitrile, hydronitrate | 98 | 94 | 92 |
| 2-(4-chlorophenyl)-2-cyclopentyloxy-3-(imidazol-1-yl)-propanenitrile | 100 | 100 | 100 |
| 2-(4-chlorophenyl)-2-cyclopentyloxy-3-(imidazol-1-yl)-propanenitrile, hydronitrate | 100 | 100 | 100 |
| 2-(4-chlorophenyl)-2-cyclopentyloxy-3-(1,2,4-triazol-1-yl)-propanenitrile | 100 | 100 | 100 |
| 2-(4-chlorophenyl)-2-cyclopentyloxy-3-(1,2,4-triazol-1-yl)-propanenitrile, hydronitrate | 100 | 100 | 100 |

The composition according to the invention is provided as a 10% or 20% formulation dispersible in water.

Example 43

Effect of Prophylactic Leaf Treatment Against *Erysiphe Cichoracearum* with Pumpkin Plants in a Greenhouse.

Pumpkin plants sprayed dripping wet with the given active substance concentrations are inoculated by means of dusting with dry mildew spores of *Erysiphe cichoracearum*, after drying of the spray coatings, and then incubated in a greenhouse at 24° C., together with innoculated but untreated control plants. After one week, the infected leaf surface is estimated in percentage of the total leafe surface.

The designation "S" in the table signifies that the fungicidal activity is also accompanied by a growth of the plants (after the treatment) and is positively determined. That is, the active substances are transported systematically into the growth area of the plants, and there to, provide 100% activity against mildew.

| Compounds According to the Invention | % Activity Against Erysiphe cichoracearum with active substance concentration | |
|---|---|---|
| | 5 | 0.5 ppm |
| 2-cyclopentyloxy-3-(imidazol-1-yl)-2-(2-methylphenyl)-propanenitrile, hydronitrate | 100s | 100 |
| 2-cyclopentyloxy-2-(2-methylphenyl)-3-(1,2,4-triazol-1-yl)-propanenitrile, hydronitrate | 100s | 100s |
| 2-cyclohexyloxy-3-(imidazol-1-yl)-2-(2-methylphenyl)-propanenitrile, hydronitrate | 100s | 100 |
| 2-cyclohexyloxy-2-(2-methylphenyl)-3-(1,2,4-trizol-1-yl)-propanenitrile, hydronitrate | 100s | 100s |
| 2-cyclohexyloxy-3-(imidazol-1-yl)-2-(2-methylphenyl)-propanenitrile | 100s | 100 |
| 2-cyclohexyloxy-2-(2-methylphenyl)-3-(1,2,4-triazol-1-yl)-propanenitrile | 100s | 100s |
| 2-cyclopentyleoxy-3-(imidazol-1-yl)-2-(2-methylphenyl)-propanenitrile | 100s | 100s |
| 2-cyclopentyloxy-2-(2-methylphenyl)-3-(1,2,4-triazol-1-yl)-propanenitrile | 100s | 100s |
| 2-cyclohexyloxy-3-(imidazol-1-yl)-2-phenyl-propanenitrile | 100s | 100s |

| Compounds According to the Invention | % Activity Against *Erysiphe cichoracearum* with active substance concentration | | |
|---|---|---|---|
| | 5 | 0.5 | ppm |
| 2-cyclohexyloxy-3-(imidazol-1-yl)-2-phenyl-propanenitrile, hydronitrate | 100s | 100 | |
| 2-(2-chlorophenyl)-2-cyclohexyloxy-3-(imidazol-1-yl)-propanenitrile | 100 | 100 | |
| 2-(2-chlorophenyl)-2-cyclohexyloxy-3-(imidazol-1-yl)-propanenitrile, hydronitrate | 100 | 100 | |
| 2-cyclohexyloxy-2-phenyl-3-(1,2,4-triazol-1-yl)-propanenitrile | 100 | 100 | |
| 2-(2-chlorophenyl)-2-cyclohexyloxy-3-(1,2,4-triazol-1-yl)-propanenitrile | 100 | 100 | |
| 2-(2-chlorophenyl)-2-cyclohexyloxy-3-(1,2,4-triazol-1-yl)-propanenitrile, hydronitrate | 100 | 100 | |
| 2-cyclopentyloxy-3-(imidazol-1-yl)-2-phenyl-propanenitrile | 100 | 100 | |
| 2-cyclopentyloxy-3-(imidazol-1-yl)-2-phenyl-propanenitrile, hydronitrate | 100 | 100 | |
| 2-(2-chlorphenyl)-2-cyclopentyloxy-3-(imidazol-1-yl)-propanenitrile | 100 | 100 | |
| 2-(2-chlorophenyl)-2-cyclopentyloxy-3-(imidazol-1-yl)-propanenitrile, hydronitrate | 100 | 97 | |
| 2-cyclopentyloxy-2-phenyl-3-(1,2,4-triazol-1-yl)-propanenitrile | 100 | 100 | |
| 2-cyclopentyloxy-2-phenyl-3-(1,2,4-triazol-1-yl)-propanenitrile, hydronitrate | 100 | 100 | |
| 2-(2-chlorophenyl)-2-cyclopentyloxy-3-(1,2,4-triazol-1-yl)-propanenitrile | 97 | 95 | |
| 2-(2-chlorophenyl)-2-cyclopentyloxy-3-(1,2,4-triazol-1-yl)-propanenitrile, hydronitrate | 100 | 100 | |
| 2-cyclohexyloxy-2-(2,4-dichlorophenyl)-3-(imidazol-1-yl)-propanenitrile | 100 | 100 | |
| 2-cyclohexyloxy-2-(2,4-dichlorophenyl)-3-(imidazol-1-yl)-propanenitrile, hydronitrate | 100 | 98 | |
| 2-(4-chlorophenyl)-2-cyclohexyloxy-3-(1,2,4-triazol-1-yl)-propanenitrile | 100 | 100 | |
| 2-(4-chlorophenyl)-2-cyclohexyloxy-3-(1,2,4-triazol-1-yl)-propanenitrile, hydronitrate | 100 | 100 | |
| 2-cyclohexyloxy-2-(2,4-dichlorophenyl)-3-(1,2,4-triazol-1-yl)-propanenitrile | 100 | 100 | |
| 2-cyclohexyloxy-2-(2,4-dichlorophenyl)-3-(1,2,4-triazol-1-yl)-propanenitrile, hydronitrate | 100 | 96 | |
| 2-(4-chlorophenyl)-2-cyclopentyloxy-3-(imidazol-1-yl)-propanenitrile | 100 | 100 | |
| 2-(4-chlorophenyl)-2-cyclopentyloxy-3-(imidazol-1-yl)-propanenitrile, hydronitrate | 100 | 100 | |
| 2-(4-chlorophenyl)-2-cyclopentyloxy-3-(1,2,4-triazol-1-yl)-propanenitrile | 100s | 100 | |
| 2-(4-chlorophenyl)-2-cyclopentyloxy-3-(1,2,4-triazol-1-yl)-propanenitrile, hydronitrate | 100s | 100 | |
| 2-cyclohexyloxy-2-phenyl-3-(1,2,4-triazol-1-yl)-propanenitrile hydronitrate | 100 | 100 | |
| 2-(4-chlorophenyl)-2-cyclohexyloxy-3-(imidazol-1-yl)-propanenitrile, hydronitrate | 100 | 100 | |
| Comparison agent | 20 | 4 | ppm |
| 2-(1-methyl-n-heptyl)-4,6-dinitrophenol-crotonate | 99.5 | 98.5 | |

The compositions are provided as 20% formulations dispersible in water.

Example 44

Effect of Prophylactic Treatment Against Dwarf Rust *Puccinia Hordei* with Barley in a Climatized Plant-Growth Chamber.

Young barley plants in the stage of the first leaves are sprayed wet with the given concentrations. After drying of the spray coatings, the treated plants as well as untreated control plants are innoculated by means of stroking over with dwarf rust-infected plants. The test plants are then placed in a plant-growth chamber. The plants are there cultivated for a period of ten days at 15° C., during the first two days of which a nearly moisture-saturated air atmosphere is provided. Then the percent-portion of rust-infected leaf surface is estimated.

| Compounds According to the Invention | % Activity Against *Puccinia hordei* with active Substance Concentration | | | |
|---|---|---|---|---|
| | 500 | 250 | 25 | ppm |
| 2-cyclopentyloxy-3-(imidazol-1-yl)-2-(2-methylphenyl)-propanenitrile, hydronitrate | 100 | 100 | >90 | |
| 2-cyclopentyloxy-2-(2-methylphenyl)-3-(1,2,4-triazol-1-yl)-propanenitrile, hydronitrate | 100 | 98 | — | |
| 2-cyclohexyloxy-3-(imidazol-1-yl)-2-(2-methyphenyl)-propanenitrile, hydronitrate | 100 | >90 | — | |
| 2-cyclohexyloxy-2-(2-methylphenyl)-2-(1,2,4-triazol-1-yl)-propanenitrile, hydronitrate | 100 | — | — | |
| 2-cyclohexyloxy-3-(imidazol-1-yl)-2-(2-methylphenyl)-propanenitrile | 100 | — | — | |
| 2-cyclohexylox-2-(2-methylphenyl)-3-(1,2,4-triazol-1-yl)-propanenitrile | 100 | — | — | |
| 2-cyclopentyloxy-3-(imidazol-1-yl)-2-(2-methylphenyl)-propanenitrile | 100 | 100 | — | |
| 2-cyclopentyloxy-2-(2-methylphenyl)-3-(1,2,4-triazol-1-yl)-propanenitrile | 100 | 100 | — | |
| 2-cyclohexyloxy-3-(imidazol-1-yl)-2-phenyl-propanenitrile | 100 | 100 | — | |
| 2-cyclohexyloxy-3-(imidazol-1-yl)-2-phenyl-propanenitrile, hydronitrate | — | 95 | — | |
| 2-(2-chlorophenyl)-2-cyclohexyloxy-3-(imidazol-1-yl)-propanenitrile | 100 | 100 | — | |
| 2-(2-chlorophenyl)-2-cyclohexyloxy-3-(imidazol-1-yl)-propanenitrile, hydronitrate | — | 98 | — | |
| 2-cyclohexyloxy-2-phenyl-3-(1,2,4-triazol-1-yl)-propanenitrile | — | 98 | — | |
| 2-cyclohexyloxy-2-phenyl-3-(1,2,4-triazol-1-yl)-propanenitrile, hydronitrate | 100 | 100 | — | |
| 2-(4-chlorophenyl)-2-cyclo- | 100 | 100 | 90 | |

-continued

| Compounds According to the Invention | % Activity Against *Puccinia hordei* with active Substance Concentration | | | |
|---|---|---|---|---|
| | 500 | 250 | 25 | ppm |
| hexyloxy-3-(imidazol-1-yl)-propanenitrate, hydronitrate | | | | |
| 2-(2-chlorophenyl)-2-cyclohexyloxy-3-(1,2,4-triazol-1-yl)-propanenitrile, hydronitrate | — | 95 | — | |
| 2-cyclopentyloxy-3-(imidazol-1-yl)-2-phenyl-propanenitrile | 100 | 100 | 90 | |
| 2-cyclopentyloxy-3-(imidazol-1-yl)-2-phenyl-propanenitrile, hydronitrate | 100 | 100 | — | |
| 2-(2-chlorophenyl)-2-cyclopentyloxy-3-(imidazol-1-yl)-propanenitrile | — | 95 | 93 | |
| 2-(2-chlorophenyl)-2-cyclopentyloxy-3-(imidazol-1-yl)-propanenitrile, hydronitrate | 100 | 100 | 85 | |
| 2-cyclopentyloxy-2-phenyl-3-(1,2,4-triazol-1-yl)-propanenitrile | 100 | 100 | 95 | |
| 2-cyclopentyloxy-2-phenyl-3-(1,2,4-triazol-1-yl)-propanenitrile, hydronitrate | — | 95 | — | |
| 2-(2-chlorophenyl)-2-cyclopentyloxy-3-(1,2,4-triazol-1-yl)-propanenitrile | 100 | 100 | 85 | |
| 2-cyclohexyloxy-2-(2,4-dichlorophenyl)-3-(imidazol-1-yl)-propanenitrile | 100 | 100 | 85 | |
| 2-cyclohexyloxy-2-(2,4-dichlorophenyl)-3-(imidazol-1-yl)-propanenitrile, hydronitrate | 100 | 100 | — | |
| 2-(4-chlorophenyl)-2-cyclohexyloxy-3-(1,2,4-triazol-1-yl)-propanenitrile | 100 | 100 | — | |
| 2-(4-chlorophenyl)-2-cyclohexyloxy-3-(1,2,4-triazol-1-yl)-propanenitrile, hydronitrate | 100 | 100 | 95 | |
| 2-cyclohexyloxy-2-(2,4-dichlorophenyl)-3-(1,2,4-triazol-1-yl)-propanenitrile | 100 | 100 | — | |
| 2-cyclohexyloxy-2-(2,4-dichlorophenyl)-3-(1,2,4-triazol-1-yl)-propanenitrile, hydronitrate | — | 95 | — | |
| 2-(4-chlorophenyl)-2-cyclopentyloxy-3-(imidazol-1-yl)-propanenitrile | 100 | 100 | 100 | |
| 2-(4-chlorophenyl)-2-cyclopentyloxy-3-(imidazol-1-yl)-propanenitrile, hydronitrate | 100 | 100 | 100 | |
| 2-(4-chlorophenyl)-2-cyclopentyloxy-3-(1,2,4-triazol-1-yl)-propanenitrile | 100 | 100 | 100 | |
| 2-(4-chlorophenyl)-2-cyclopentyloxy-3-(1,2,4-triazol-1-yl)-propanenitrile, hydronitrate | 100 | 100 | 100 | |
| Comparison Agent | | | | |
| 2,3-dihydro-5-carboxanilido-6-methyl-1,4-oxathiine-4,4-dioxide | | 97.5 | <75 | |

The compositions are provided at 10% or 20% formulations dispersible in water.

Example 45

Effect of Prophylactic Leaf Treatment Against the Leaf-Spot Disease *Cerospora Beticola* in Sugar Beets (*Beta Vulgaris*).

Sugar beet plants with four well developed leaf flakes are sprayed so as to become dripping wet with the given concentrations. After drying of the spray coatings, the treated plants as well as untreated control plants are uniformly sprayed with a suspension of 15,000 cerocospora spores per ml. At 26° C. and under water vapor-saturated air, the plants are incubated four days in a greenhouse. Thereafter, at a temperature of about 22° C. they are kept an additional ten days in a greenhouse. The portion of infected leaf surface is estimated.

| Compounds According to the Invention | % Activity against *Cercospora beticola* with Active Substance Concentration | | |
|---|---|---|---|
| | 500 | 100 | ppm |
| 2-cyclohexyloxy-3-(imidazol-1-yl)-2-phenyl-propanenitrile | 100 | — | |
| 2-cyclohexyloxy-3-(imidazol-1-yl)-2-phenyl-propanenitrile hydronitrate | 99 | 93 | |
| 2-(2-chlorophenyl)-2-cyclohexyloxy-3-(imidazol-1-yl)-propanenitrile | 93 | — | |
| 2-(2-chlorophenyl)-2-cyclohexyloxy-3-(imidazol-1-yl)-propanenitrile, hydronitrate | 97 | 86 | |
| 2-cyclohexyloxy-2-phenyl-3-(1,2,4-triazol-1-yl)-propanenitrile | 100 | 90 | |
| 2-cyclohexyloxy-2-phenyl-3-(1,2,4-triazol-1-yl)-propanenitrile, hydronitrate | 100 | 100 | |
| 2-(2-chlorophenyl)-2-cyclohexyloxy-3-(1,2,4-triazol-1-yl)-propanenitrile | 100 | 83 | |
| 2-(2-chlorophenyl)-2-cyclohexyloxy-3-(1,2,4-triazol-1-yl)-propanenitrile, hydronitrate | 100 | — | |
| 2-cyclopentyloxy-3-(imidazol-1-yl)-2-phenyl-propanenitrile | 100 | 99 | |
| 2-cyclopentyloxy-3-(imidazol-1-yl)-2-phenyl-propanenitrile hydronitrate | 100 | 96 | |
| 2-(2-chlorophenyl)-2-cyclopentyloxy-3-(imidazol-1-yl)-propanenitrile, hydronitrate | 100 | 99 | |
| 2-cyclopentyloxy-2-phenyl-3-(1,2,4-triazol-1-yl)-propanenitrile | 100 | 100 | |
| 2-cyclopentyloxy-2-phenyl-3-(1,2,4-triazol-1-yl)-propanenitrile, hydronitrate | 100 | 100 | |
| 2-(2-chlorophenyl)-2-cyclopentyloxy-3-(1,2,4-triazol-1-yl)-propanenitrile | 100 | 100 | |
| 2-(2-chlorophenyl)-2-cyclopentyleoxy-3-(1,2,4-triazol-1-yl)-propanenitrile, hydronitrate | 100 | 100 | |
| 2-cyclohexyloxy-2-(2,4-dichlorophenyl)-3-(imidazol-1-yl)-propanenitrile | 99 | 93 | |
| 2-cyclohexyloxy-2-(2,4-dichlorophenyl)-3-(imidazol-1-yl)-propanenitrile, hydronitrate | 93 | 80 | |
| 2-(4-chlorophenyl)-2-cyclohexyloxy-3-(1,2,4-triazol-1-yl)-propanentrile | 100 | 84 | |
| 2-(4-chlorophenyl)-2-cyclohexyloxy-3-(1,2,4-triazol-1-yl)-propanenitrile, hydronitrate | 100 | 82 | |
| 2-cyclohexyloxy-2-(2,4-dichlorophenyl)-3-(1,2,4-triazol-1-yl)-propanenitrile | 100 | — | |
| 2-(4-chlorophenyl)-2-cyclopentyloxy-3-(imidazol-1-yl)-propanenitrile | 100 | 96 | |
| 2-(4-chlorophenyl)-2-cyclopentyloxy-3-(imidazol-1-yl)-peopanenitrile, hydronitrate | 100 | 100 | |
| 2-(4-chlorophenyl)-2-cyclo- | 100 | 100 | |

| Compounds According to the Invention | % Activity against *Cercospora beticola* with Active Substance Concentration | |
|---|---|---|
| | 500 | 100 ppm |
| pentyloxy-3-(1,2,4-triazol-1-yl)-propanenitrile | | |
| 2-(4-chlorophenyl)-2-cyclopentyloxy-3-(1,2,4-triazol-1-yl)-propanenitrile, hydronitrate | 100 | 96 |

The compounds are provided as 10% or 20% formulations dispersible in water.

| | | |
|---|---|---|
| 2-(2-chlorophenyl)-2-cyclopentyloxy-3-(imidazol-1-yl)-propanenitrile | 100 | 99 |

Example 46

Effect of Prophylactic Spray Treatment Against *Fusarium Colmorum* in Club Millet (*Setaria Italica*).

Young millet plants of three to four cm height are sprayed dripping wet with the given concentrations. After drying of the spray coatings, the treated plants as well as untreated control plants are sprayed with a 30% biomalt-containing aqueous suspension of fusarium spores (800,000 per ml), and then incubated moist in a greenhouse at 20°–22° C. After six days, the percent portion of infected leaf surface is estimated.

| Compounds According to the Invention | % Activity against *Fusarium culmorum* with Active Substance Concentration |
|---|---|
| | 500 ppm |
| 2-cyclopentyloxy-3-(imidazol-1-yl)-2-(2-methylphenyl)-propanenitrile, hydronitrate | 97 |
| 2-cylcopentyloxy-2-(2-methylphenyl)-3-(1,2,4-triazon-1-yl)-propanenitrile, hydronitrate | 97 |
| 2-cyclohexyloxy-3-(imidazol-1-yl)-2-(2-methylphenyl)-propanenitrile, hydronitrate | 96 |
| 2-cyclohexyloxy-2-(2-methylphenyl)-3-(1,2,4-triazol-1-yl)-propanenitrile, hydronitrate | 91 |
| 2-cyclohexyloxy-3-(imidazol-1-yl)-2-(2-methylphenyl)-propanenitrile | 97 |
| 2-cyclohexyloxy-2-(2-methylphenyl)-3-(1,2,4-triazol-1-yl)-propanenitrile | 96 |
| 2-cyclopentylxoy-3-(imidazol-1-yl)-2-(2-methylphenyl)-propanenitrile | 99 |
| 2-cyclopentyloxy-2-(methylphenyl)-3-(1,2,4-triazol-1-yl)-propanenitrile | 97 |
| 2-cyclopentyloxy-3-(imidazol-1-yl)-2-phenyl-propanenitrile | 95 |
| 2-cyclopentyloxy-3-(imidazol-1-yl)-2-phenyl-propanenitrile, hydronitrate | 90 |
| 2-(2-chlorophenyl)-2-cyclopentyloxy-3-(imidazol-1-yl)-propanenitrile | 90 |
| 2-(2-chlorophenyl)-2-cyclopentyloxy-3-(imidazol-1-yl)-propanenitrile, hydronitrate | 93 |
| 2-(4-chlorophenyl)-2-cyclopentyloxy-3-(imidazol-1-yl)-propanenitrile | 97 |
| 2-(4-chlorophenyl)-2-cyclopentyl-oxy-3-(imidazol-1-yl)-propanenitrile, hydronitrate | 95 |
| 2-(4-chlorophenyl)-2-cyclopentyloxy-3-(1,2,4-triazol-1-yl)-propanenitrile | 90 |
| 2-(4-chlorophenyl)-2-cyclopentyloxy-3-(1,2,4-triazol-1-yl)-propanenitrile, hydronitrate | 95 |

The compounds are provided as 10% or 20% formulations dispersible in water.

Example 47

Effect of Prophylactic Spray Treatment Against *Botrytis Cinerea* in Tomato Plants.

Young tomato plants with at least two well developed leaf flakes are sprayed dripping wet with the given active substance concentrations. After drying of the spray coatings, the treated plants as well as untreated control plants are innoculated by means of spraying of a suspension of about one million botrytis spores per ml fruit juice solution. Subsequently the plants are incubated moist in a greenhouse at about 20° C. After crumbling of the untreated plants (=100% infection) the degree of infection of the treated plants is determined.

| Compounds According to the Invention | % Activity Against *Botrytis cinerea* with Active Substance Concentration |
|---|---|
| | 250 ppm |
| 2-(4-chlorophenyl)-2-cyclopentyloxy-3-(imidazol-1-yl)-propanenitrile | 80 |
| 2-(4-chlorophenyl)-2-cyclopentyloxy-3-(imidazol-1-yl)-propanenitrile, hydronitrate Comparison Agent from DE-OS 26 04 047 | 80 |
| 2-(imidazol-1-yl-methyl)-2-phenyl-hexanenitrile hydronitrate | 5 |

Example 48

Effect of Prophylactic Spray Treatment Against *Helminthosporium Teres* (*pyrenophora teres*) in Barley.

Young barley plants in the stage of the first leaves are sprayed dripping wet with the given concentrations. After drying of the spray coatings, the treated plants as well as untreated control plants are sprayed with an aqueous conidiospore suspension (about 50,000 per ml) of *Helminthosporium Teres* and then incubated in a moisture-chamber in a greenhouse for a period of two days at 20°–22° C. Thereafter the plants are cultivated in a greenhouse at about 20°–22° C. One week after the innoculation, the percent portion of infected leaf surface is estimated.

| Compounds According to the Invention | % Activity Against *Helminthosporium Teres* with Active Substance Concentration |
|---|---|
| | 500 ppm |
| 2-cyclopentyloxy-3-(imidazol-1-yl)-2-(2-methylphenyl-propanenitrile, hydronitrate | 80 |
| 2-cyclohexyloxy-3-(imidazol-1-yl)-2- | 80 |

| Compounds According to the Invention | % Activity Against *Helminthosporium Teres* with Active Substance Concentration | |
|---|---|---|
| | 500 | ppm |
| (2-methylphenyl)-propanenitrile | | |
| 2-cyclohexyloxy-2-(2-methylphenyl)-3-(1,2,4-triazol-1-yl)-propanenitrile | 80 | |

Example 49

Effect of Prophylactic Spray Treatment Against *Cochliobolus Miyabeanus* in Rice Plants.

Young rice plants in the stage of the start of the second leaves are sprayed dripping wet with the given concentrations. After drying of the spray coatings, the treated plants as well as untreated control plants are sprayed with an aqueous conidia suspension (about 250,000 per ml) of the fungus, and then incubated moist in a greenhouse at about 24° C. After four days the percent portion of the infected leaf surface is noted.

| Compounds According to the Invention | % Activity Against *Cochliobolus miyabeanus* with Active Substance Concentration | |
|---|---|---|
| | 500 | ppm |
| 2-cyclopentyloxy-3-(imidazol-1-yl)-2-(2-methylphenyl)-propanenitrile, hydronitrate | 80 | |
| 2-cyclopentyloxy-2-(2-methylphenyl)-3-(1,2,4-triazol-1-yl)-propanenitrile, hydronitrate | 80 | |
| 2-cyclohexyloxy-3-(imidazol)-1-yl)-2-(2-methylphenyl)-propanenitrile, hydronitrate | 80 | |
| 2-cyclohexyloxy-2-(2-methyl-pehnyl)-3-(1,2,4-triazol-1-yl)-propanenitrile, hydronitrate | 80 | |
| 2-cyclohexyloxy-3-(imidazol-1-yl)-2-(2-methylphenyl)-propanenitrile | 80 | |
| 2-cyclohexyloxy-2-(2-methyl-phenyl)-3-(1,2,4-triazol-1-yl)-propanenitrile | 80 | |
| 2-cyclopentyloxy-3-(imidazol-1-yl)-2-(2-methylphenyl)-propanenitrile | 80 | |

Example 50

Effect of Prophylactic Spray Treatment Against *Phytophthora Infestans* in Tomato Plants.

Young tomato plants with at least two well developed leaf flakes are sprayed dripping wet. After drying of the spray coatings, the treated plants as well as unctreated control plants are sprayed with an aqueous suspension of about 80,000 phytophthora sporangia per ml, the suspension having been incubated for two hours at 11° C. The plants are then incubated moist in a greenhouse at about 18° C. After five days the percent portion of infected leaf surface is estimated.

| Compound According to the Invention | % Activity Against *Phytophthora infestans* with Active Substance Concentration | |
|---|---|---|
| | 500 | ppm |
| 2-cyclohexyloxy-2-phenyl-3-(1,2,4-triazol-1-yl)-propanenitrile | 91 | |

Example 51

Activity Against Apple Scab (*Venturia inequalis*), Prophylactic and Curative.

The five youngest leaves of apple shoots planted in free acreage are treated dripping wet. After drying of the spray coatings, these shoots as well as untreated shoots are sprayed with a suspension of 320,000 conidiospore of the fungus per ml 3% glucose solution in distilled water, and then confined for a period of 53 hours in polyethylene sacks under shade. Eight days after the innoculation a number of the untreated, innoculated shoots are subjected to a curative treatment (dripping wet). Five weeks after the innoculation the percent degree of scab covering on the leaf surfaces is estimated.

| Compound According to the Invention | % Activity Against Apple Scab with Active Substance Concentration | |
|---|---|---|
| | 750 ppm Prophylactic | Curative |
| 2-cyclopentyloxy-3-(imidazol-1-yl)-2-(2-methylphenyl)-propanenitrile | 100 | 86 |
| Control (untreated) | 35% infection | |

| Compounds According to the Invention | % Activity Against Apple Scab with Active Substance Concentration | |
|---|---|---|
| | 300 ppm Prophylactic | Curative |
| 2-cyclopentyloxy-3-(imidazol-1-yl)-2-(2-methylphenyl)-propanenitrile | 86 | — |
| 2-cyclohexyloxy-3-(imidazol-1-yl)-2-phenyl-propanenitrile | 98 | — |
| 2-cyclohexyloxy-3-(imidazol-1-yl)-2-phenyl-propanenitrile, hydronitrate | 90 | — |
| 2-cyclopentyloxy-3-(imidazol-1-yl)-2-phenyl-propanenitrile | 97 | 81 |
| 2-cyclopentyloxy-3-(imidazol-1-yl)-2-phenyl-propanenitrile, hydronitrate | 91 | 90 |
| 2-cyclopentyloxy-2-phenyl-3-(1,2,4-triazol-1-yl)-propanenitrile | 100 | 95 |
| 2-cyclopentyleoxy-2-phenyl-3-(1,2,4-triazol-1-yl)-propanenitrile, hydronitrate | 100 | 90 |
| 2-(2-chlorophenyl)-2-cyclopentyloxy-3-(1,2,4-triazol-1-yl)-propanenitrile | 98 | 73 |
| 2-(2-chlorophenyl)-2-cyclopentyloxy-3-(1,2,4-triazol-1-yl)-propanenitrile, hydronitrate | 88 | — |
| 2-cychlohexy-2-(2,4-dichlorophenyl)-3-(imidazol-1-yl)-propanenitrile | 84 | — |
| 2-(4-chlorophenyl)-2-cyclohexyloxy-3-(1,2,4-triazol-1-yl)-propaneitrile | 100 | 93 |
| 2-(4-chlorophenyl)-2-cyclohexyloxy-3-(1,2,4-triazol- | 100 | 99.5 |

| -continued | | |
|---|---|---|
| 1-yl)-propanenitrile, hydronitrate | | |
| 2-(4-chlorophenyl)-2-cyclopentyloxy-3-(imidazol-1-yl)-propanenitrile | 96 | 99 |
| 2-(4-chlorophenyl)-2-cyclopentyloxy-3-(imidazol-1-yl)-propanenitrile, hydronitrate | 89 | 95 |
| 2-(4-chlorophenyl)-2-cyclopentyloxy-3-(1,2,4-triazol-1-yl)-propanenitrile | 99.5 | 94 |
| 2-(4-chlorophenyl)-2-cyclopentylxoy-3-(1,2,4-triazol-1-yl)-propanenitrile, hydronitrate | 100 | 99 |

The following operational examples serve for illustration of use possibilities of the compounds according to the present invention as growth regulators:

Example 52

Growth-regulatory Effect with Sugar Beets.

Sugar beets are treated in a pre-germination technique with a calculated 0.5 kg active substances per ha, and then further cultivated in a greenhouse. Eight days after the application, the percent restraint of growth is determined as the influence of the preparation.

| Compounds According to the Invention | Percent Growth Restraint |
|---|---|
| 2-cyclohexyloxy-2-(2-methylphenyl)-3-(1,2,4-triazol-1-yl)-propanenitrile, hydronitrate | 40 |
| 2-cyclohexyloxy-2-(2-methylphenyl)-3-(1,2,4-triazol-1-yl)-propanenitrile | 20 |
| Control | 0 |

The treatment of the plants leads to a growth restraint and a dark green coloration of the leaves.

Example 53

Growth Regulation with Sugar Beets and Corn.

Corn and sugar beets are placed in a greenhouse after a pre-germination spraying with the substances according to the present invention. Eleven days after the treatment, growth-regulatory effects are determined by way of the percent growth restraint. 0.5 kg active substance per ha led to the following results:

| Compounds According to the Invention | Percent Growth Restraint | |
|---|---|---|
| | Corn | Sugar Beets |
| 2-(2-chlorophenyl)-2-cyclohexyloxy-3-(imidazol-1-yl)-propanenitrile | 14 | 14 |
| 2-(2-chlorophenyl)-2-cyclohexyloxy-3-(imidazol-1-yl)-propanenitrile, hydronitrate | 21 | 14 |
| 2-(4-chlorophenyl)-2-cyclohexyloxy-3-(imidazol-1-yl)-propanenitrile, hydronitrate | 14 | 14 |
| 2-(4-chlorophenyl)-2-cyclopentyloxy-3-(imidazol-1-yl)-propanenitrile | 21 | 29 |
| 2-(4-chlorophenyl)-2-cyclopentyloxy-3-(1,2,4-triazol-1-yl)-propanenitrile | 36 | 57 |

| Compounds According to the Invention | Percent Growth Restraint | |
|---|---|---|
| | Corn | Sugar Beets |
| Control | 0 | 0 |

The results show that the substances according to the present invention clearly restrain the longitudinal growth of the treated plants.

Example 54

Effect of Prophylactic Leaf Treatment Against *Plasmopara viticola* with Grape Plants in a Greenhouse.

Young grape plants with about 5 to 8 leaves are sprayed dripping wet with 500 ppm active substance concentration. After drying of the spray coatings, the undersides of the leaves are sprayed with an aqueous deposit of sporangia of the fungus (about 55,000 per ml), and then incubated in a greenhouse at 22°–24° C. in an atmosphere as water vapor-saturated as possible.

From the second day, the air moisture is brought back to a normal level (30 to 70% saturation) for a period of 3–4 days, and then held at water vapor-saturation for 1 further day. Subsequently each leaf is evaluated insofar as the percent portion of fungus-infected surface, and the average per treatment is used for determination of the fungicidal activity as described above.

| Compounds According to the Invention | Activity Against *Plasmopara viticola* |
|---|---|
| 2-cyclopentyloxy-3-(imidazol-1-yl)-2-(2-methylphenyl)-propaneitrile, hydronitreat | 89 |
| 2-cyclopentyloxy-2-(2-methylphenyl)-3-(1,2,4-triazol-1-yl)-propanenitrile, hydronitrate | 84 |
| 2-cyclohexyloxy-3-(imidazol-1-yl)-2-(2-methylphenyl)-propanenitrile, hydronitrate | 100 |
| 2-cyclohexyloxy-2-(2-methylphenyl)-3-(1,2,4-triazol-1-yl)-propanenitrile, hydronitrate | 85 |
| 2-cyclohexyloxy-2-phenyl-3-(1,2,4-triazol-1-yl)-propanenitrile | 91 |
| 2-cyclohexyloxy-3-(imidazol-1-yl)-2-(2-methylphenyl)-propanenitrile | 95 |
| 2-cyclohexyloxy-2-(2-methylphenyl)-3-(1,2,4-triazol-1-yl)-propanenitrile | 91 |
| 2-cyclopentyloxy-3-(imidazol-1-yl)-2-(2-methylphenyl)-peopanenitrile | 98 |
| 2-cyclopentyloxy-3-(imidazol-1-yl)-2-phenyl-propanenitrile | 100 |
| 2-cyclopentyloxy-3-(imidazol-1-yl)-2-phenyl-propanenitrile, hydronitrate | 73 |
| 2-(2-chlorophenyl)-2-cyclopentyloxy-3-(imidazol-1-yl)-propanenitrile | 90 |
| 2-(2-chlorophenyl)-2-cyclopentyloxy-3-(imidazol-1-yl)-propanenitrile, hydronitrate | 97 |
| 2-cyclopentyloxy-2-phenyl-3-(1,2,4-triazol-lyl)-propanenitrile | 95 |
| 2-cyclopentyloxy-2-phenyl-3-(1,2,4-triazol-1-yl)-propanenitrile, hydronitrate | 98 |
| 2-(2-chlorophenyl)-2-cyclopentyloxy-3-(1,2,4-triazol-1-yl)-propanenitrile | 98 |
| 2-(4-chlorophenyl)-2-cyclo- | 99.5 |

| Compounds According to the Invention | Activity Against *Plasmopara viticola* |
|---|---|
| pentyloxy-3-(imidazol-1-yl)-propanenitrile | |
| 2-(4-chlorophenyl)-2-cyclopentyloxy-3-(imidazol-1-yl)-propanenitrile, hydronitrate | 100 |
| 2-(4-chlorophenyl)-2-cyclopentyloxy-3-(1,2,4-triazol-1-yl)-poropanenitrile | 97 |
| 2-(4-chlorophenyl)-2-cyclopentyloxy-3-(1,2,4-triazol-1-yl)-propanenitrile, hydronitrate | 85 |

The agents according to the invention are provided as 10% or 20% formulations dispersible in water.

Example 55

Activity in vitro Against *Mucor spec.* of Soybeans.

Aqueous preparations of the active substances are mixed with sterilized, liquid agar nutrient base (2% biomalt, 2% agar) at about 45° C. in such manner that the mixture contains 250 ppm active substance. The mixture is then placed in polystyrene petri dishes of 8.5 cm diam. to a height of 5 mm. After cooling of the nutrient base, each petri dish is provided with a 5 mm diam. agar piece overgrown with Mucor. Per treatment, two dishes and also four untreated dishes are inoculated.

After five days incubation at 22° C. in the dark, the colony diameters are measured and after removal of the inoculate quantity of 5 mm, employed as follows for calculation of the fungicidal activity:

$$100 - \frac{\text{Diameter without inoculate in treated} \cdot 100}{\text{Diameter without inoculate in untreated}} = \% \text{ activity}$$

| Compounds According to the Invention | % Activity Against Mucor Spec. |
|---|---|
| 2-cyclopentyloxy-2-(2-methylphenyl)-3-(1,2,4-triazol-1-yl)-propanenitrile, hydronitrate | 80 |
| 2-cyclopentyloxy-3-(imidazol-1-yl)-2-(2-methylphenyl)-propanenitrile | 75 |
| 2-cyclohexyloxy-2-phenyl-3-(1,2,4-triazol-1-yl)-propanenitrile | 100 |
| 2-cyclopentyloxy-3-(imidazol-1-yl)-2-phenyl-propanenitrile | 95 |
| 2-(2-chlorophenyl)-2-cyclopentyloxy-3-(imidazol-1-yl)-propanenitrile | 94 |
| 2-cyclopentyloxy-2-phenyl-3-(1,2,4-triazol-1-yl)-propanenitrile | 100 |
| 2-cyclopentyloxy-2-phenyl-3-(1,2,4-triazol-1-yl)-propanenitriel, hydronitrate | 75 |
| 2-(2-chlorophenyl)-2-cyclopentyloxy-3-(1,2,4-triazol-1-yl)-propanenitrile | 98 |
| 2-(4-chlorophenyl)-2-cyclopentyloxy-3-(imidazol-1-yl)-propanenitrile | 100 |
| 2-(4-chlorophenyl)-2-cyclopentyloxy-3-(imidazol)1-yl)-propanenitrile, hydronitrate | 77 |
| 2-(4-chlorophenyl)-2-cyclopentyloxy-3-(1,2,4-triazol-1-yl)-propanenitrile | 100 |
| 2-(4-chlorophenyl)-2-cyclopentyloxy-3-(1,2,4-triazol-1-yl)-propanenitrile, hydronitrate | 87 |
| Comparison agent | |
| 2-cyano-2-methoxyiminoacetic acid ethylaminocarbonylamide | 50 |

The agents according to the invention are provided as 10% or 20% formulations dispersible in water.

Example 56

Effect in vitro Against *Pseudomonas phaseolicola* (Fat Spot Disease of Beans).

Aqueous preparations of the active substances are mixed with sterilized, liquid agar base (2% biomalt, 2% agar) at about 56° C. in such manner that the mixtures contain 50 ppm active substance. The mixtures are then placed in polystyrene petri dishes of 8.5 cm. diam. to a height of 5 mm. After cooling of the nutrient base, the middle of each petri dish is dabbed with a suspension of *pseudomonas phaseolicola* in distilled water by means of 5 mm. quantity inoculation loop. Per treatment, two dishes and four untreated dishes are inoculated. After four and one half weeks incubation at 20°-22° C. in the dark, the colony diameters are determined. After withdrawal of the inoculate quantity, the colonies are employed as follows for a calculation of bactericidal activity:

$$100 - \frac{\text{Diameter without inoculate in treated} \cdot 100}{\text{Diameter without inoculate in untreated}} = \% \text{ activity}$$

| Compounds According to the Invention | % Activity Against *Pseudomonas phaseolicola* |
|---|---|
| 2-(2-chlorophenyl)-2-cyclopentyloxy-3-(imidazol-1-yl)-propanenitrile, hydronitrate | 82 |
| 2-cyclopentyloxy-2-phenyl-3-(1,2,4-triazol-1-yl)-propanenitrile | 73 |
| 2-cyclopentyloxy-2-phenyl-3-(1,2,4-triazol-1-yl)-propanenitrile, hydronitrate | 91 |
| 2-(2-chlorophenyl)-2-cylcopentyloxy-3-(1,2,4-triazol-1-yl)-propanenitrile | 91 |
| 2-(4-chlorophenyl)-2-cyclopentyloxy-3-(imidazol-1-yl)-propanenitrile | 100 |
| 2-(4-chlorophenyl)-2-cyclopentyloxy-3-(imidazol-1-yl)-propanenitrile, hydronitrate | 100 |
| 2-(4-chlorophenyl)-2-cyclopentyloxy-3-(1,2,4-triazol-1-yl)-propanenitrile | 91 |
| 2-(4-chlorophenyl)-2-cyclopentyloxy-3-(1,2,4-triazol-1-yl)-propanenitrile, hydronitrate | 91 |
| Comparison Agent | |
| 2-cyano-2-methoxyiminoacetic acid-ethylaminocarbonylamide | 0 |

The agents according to the invention are provided as 10% or 20% formulations dispersible in water.

It will be understood that each of the elements described above, or two or more together, will also find a useful application in other types of biocidal preparation differing from the types described above.

While the invention has been illustrated and described as embodied in azolyl-propanenitriles, processes for the production of these compounds as well as biocidal compositions containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, can readily adapt it for various applications without omitting features that, from the standpoint of prior art, fairly constitute essential characteristics of the generic and specific aspects of this invention.

What is desired to be protected by Letters Patent is set forth in the appended claims.

We claim:

1. Azolyl-propanenitrile of the formula

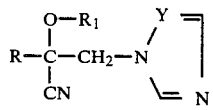   I in which

R is phenyl, methylphenyl, fluorophenyl, chlorophenyl or dichlorophenyl, $R_1$ is cyclopentyl or cyclohexyl, and Y is N or CH, or a salt thereof with nitric acid.

2. The compound according to claim 1 wherein R is 2-fluorophenyl, 3-fluorophenyl, 4-fluorophenyl, 2-chlorophenyl, 3-chlorophenyl, 4-chlorophenyl, 2,4-dichlorophenyl, 3,4-dichlorophenyl, 2,6-dichlorophenyl, 2-methylphenyl, 3-methylphenyl, or 4-methylphenyl, $R_1$ is cyclopentyl or cyclohexyl, and Y is N or CH.

3. The compound according to claim 1, 2-cyclopentyloxy-3-(imidazol-1-yl)-2-(2-methylphenyl)-propanenitrile, hydronitrate.

4. The compound according to claim 1, 2-cyclopentyloxy-3-(imidazol-1-yl)-2-phenyl-propanenitrile, hydronitrate.

5. The compound according to claim 1, 2-cyclopentyloxy-2-phenyl-3-(1,2,4-triazol-1-yl)-propanenitrile, hydronitrate.

6. The compound according to claim 1, 2-(2-chlorophenyl)-2-cyclopentyloxy-3-(1,2,4-triazol-1-yl)-propanenitrile, hydronitrate.

7. The compound according to claim 1, 2-(4-chlorophenyl)-2-cyclopentyloxy-3-(imidazol-1-yl)-propanenitrile, hydronitrate.

8. The compound according to claim 1, 2-(4-chlorophenyl)-2-cyclopentyloxy-3-(1,2,4-triazol-1-yl)-propanenitrile, hydronitrate.

9. A fungicidal, plant growth regulating and bactericidal composition comprising from 10 to 90 percent by weight of at least one compound according to claim 1 in mixture with a carrier material, with or without an adjuvant.

10. Method or protecting plants against fungi, comprising applying onto or within the locus of said plants a fungicidally-effective amount of the composition according to claim 9.

11. Method of regulating the growth of plants, comprising applying onto or within the locus of said plants a growth-regulatory-effective amount of the composition according to claim 9.

12. Method of protecting plants against bacteria, comprising applying onto or within the locus of said plants a bactericidally-effective amount of the composition according to claim 9.

* * * * *